(12) United States Patent
Shin et al.

(10) Patent No.: US 10,709,542 B2
(45) Date of Patent: Jul. 14, 2020

(54) STENT WITH IMPROVED ANTI-SLIP FUNCTION

(71) Applicants: TAEWOONG MEDICAL CO., LTD., Gyeonggi-do (KR); Kyong Min Shin, Gyeonggi-do (KR)

(72) Inventors: Kyong Min Shin, Gyeonggi-do (KR); Sung Wook Park, Gyeonggi-do (KR); Dong Su Ko, Incheon-si (KR)

(73) Assignees: TAEWOONG MEDICAL CO., LTD., Gyeonggi-do (KR); Kyong Min Shin, Gyeonggi-do (KR)

( * ) Notice: Subject to any disclaimer, the term of this patent is extended or adjusted under 35 U.S.C. 154(b) by 306 days.

(21) Appl. No.: 15/735,876

(22) PCT Filed: Jul. 6, 2016

(86) PCT No.: PCT/KR2016/007289
§ 371 (c)(1),
(2) Date: Dec. 12, 2017

(87) PCT Pub. No.: WO2017/018682
PCT Pub. Date: Feb. 2, 2017

(65) Prior Publication Data
US 2020/0030079 A1  Jan. 30, 2020

(30) Foreign Application Priority Data
Jul. 27, 2015 (KR) .................. 10-2015-0105715

(51) Int. Cl.
*A61F 2/07* (2013.01)
*A61F 2/90* (2013.01)
*A61F 2/00* (2006.01)

(52) U.S. Cl.
CPC .................. *A61F 2/07* (2013.01); *A61F 2/90* (2013.01); *A61F 2002/0081* (2013.01);
(Continued)

(58) Field of Classification Search
CPC .................. A61F 2/07; A61F 2002/072; A61F 2210/0014; A61F 2210/0076;
(Continued)

(56) References Cited

U.S. PATENT DOCUMENTS

| 5,667,523 A | * | 9/1997 | Bynon | ...................... A61F 2/07 606/194 |
| 6,010,529 A | * | 1/2000 | Herweck | ................... A61F 2/06 600/36 |

(Continued)

FOREIGN PATENT DOCUMENTS

| KR | 1020100042478 |   | 4/2010 |   |
| KR | 1020100090988 | * | 8/2010 | ............... A61F 2/86 |

(Continued)

OTHER PUBLICATIONS

Written Opinion English Language Translation of PCT/KR2016/007289 (6 pages) dated Oct. 12, 2016. (Year: 2016).*

*Primary Examiner* — Paul B Prebilic
(74) *Attorney, Agent, or Firm* — IP & T Group LLP

(57) ABSTRACT

A stent with an improved anti-slip function. The stent includes: a cylindrical stent including a plurality of openings formed by weaving wires, and a plurality of peaks, the cylindrical stent being subjected to heat treatment, wherein the cylindrical stent has a PTFE-first artificial blood vessel layer being in entire contact with an inner surface thereof, and a plurality of PTFE-second artificial blood vessel layers being in partial contact with an outer surface thereof, and the first and second artificial blood vessel layers are heat-fused together to encompass the cylindrical stent, thereby forming a plurality of first sections having a plurality of openings obstructed and a plurality of seconds sections having the plurality of openings remaining unobstructed, wherein the first sections are inserted into a lesion while pressing against (Continued)

the lesion, thereby being caught in the lesion, and the second sections are caught in the lesion meshed with the openings.

8 Claims, 6 Drawing Sheets

(52) U.S. Cl.
CPC . *A61F 2002/077* (2013.01); *A61F 2210/0014* (2013.01); *A61F 2210/0076* (2013.01); *A61F 2230/0017* (2013.01); *A61F 2230/0069* (2013.01); *A61F 2240/001* (2013.01); *A61F 2250/0037* (2013.01); *A61F 2250/0039* (2013.01)

(58) Field of Classification Search
CPC ...... A61F 2230/0069; A61F 2250/0023; A61F 2250/0026; A61F 2250/0037; A61F 2250/0038; A61F 2250/0051
See application file for complete search history.

(56) References Cited

U.S. PATENT DOCUMENTS

| | | | | |
|---|---|---|---|---|
| 6,143,022 A | * | 11/2000 | Shull | A61F 2/91 623/1.13 |
| 6,398,803 B1 | * | 6/2002 | Layne | A61F 2/07 623/1.13 |
| 6,945,991 B1 | * | 9/2005 | Brodeur | A61F 2/07 623/1.13 |
| 7,186,263 B2 | | 3/2007 | Golds et al. | |
| 2002/0026231 A1 | * | 2/2002 | Shannon | A61F 2/07 623/1.13 |
| 2002/0173836 A1 | * | 11/2002 | Pinchuk | A61F 2/90 623/1.12 |
| 2011/0319980 A1 | * | 12/2011 | Ryan | A61F 2/07 623/1.16 |
| 2017/0143467 A1 | * | 5/2017 | Myung | A61F 2/04 |

FOREIGN PATENT DOCUMENTS

| | | |
|---|---|---|
| KR | 101006990 | 1/2011 |
| KR | 101382524 | 4/2014 |
| KR | 1020150051651 | 5/2015 |
| KR | 1020150052719 | 5/2015 |

* cited by examiner

STENT WITH IMPROVED ANTI-SLIP FUNCTION

This application is a national stage application of PCT/KR2016/007289 filed on Jul. 6, 2016, which claims priority of Korean patent application number 10-2015-0105715 filed on Jul. 27, 2015. The disclosure of each of the foregoing applications is incorporated herein by reference in its entirety.

TECHNICAL FIELD

The present invention relates generally to a stent with an improved anti-slip function. More particularly, the present invention relates to a stent with an improved anti-slip function, wherein the stent is prevented from slipping at a lesion such as stenosis or occlusion occurring in a lumen of the human body such as the esophagus, the duodenum, or the bile duct due to movement of the body or an external force.

BACKGROUND ART

In general, when a lesion such as stenosis or occlusion occurs in a lumen of the body such as the esophagus, the duodenum, or the bile duct, the inherent function of the lumen that moves bodily fluids is deteriorated.

A bending-retaining coated stent capable of retaining a bending state is known, wherein the stent is configured with a plurality of rhombic openings that are formed by weaving different shape-memory alloy wires alternatively with a plurality of interlocking portions and a plurality of intersection portions such that the rhombic openings are changeable in size by an external force, and which is subjected to heat treatment to memorize a shape thereof. Then, a polytetrafluoroethylene (PTFE) tape or a similar material is wound around a plurality of sections divided in a lengthwise direction of the stent with an interval so that a coating layer of silicone or a similar material is prevented from being coated on the interlocking portions and the intersection portions comprised of the stent wound with the tape, and on the rhombic openings formed thereby. Accordingly, the interlocking portions, the intersection portions, and the rhombic openings that remain uncoated are allowed to freely change in size by an external force, thereby maintaining a bending state.

However, this stent is problematic in that the coating layer made of silicone or the like on the outside of the stent may slide at the lesion such as stenosis or occlusion due to movement of the human body or an external force.

DISCLOSURE

Technical Problem

Accordingly, the present invention has been made keeping in mind the above problems occurring in the prior art, and an object of the present invention is to provide a stent with an improved anti-slip function, wherein the stent is prevented from slipping at the lesion such as stenosis or occlusion occurring in a lumen of the body such as the esophagus, the duodenum, or the bile duct due to movement of the human body or an external force.

Technical Solution

In order to accomplish the above object, the present invention provides a stent with an improved anti-slip function, the stent being configured to widen a lesion such as stenosis or occlusion in a lumen of a body, and including: a cylindrical stent including a plurality of rhombic openings formed by weaving wires made of a super-elastic shape memory alloy in a hollow cylindrical mesh shape in an interlocking or intersecting manner, and a plurality of peaks circumferentially provided at opposite corrugated ends of the cylindrical stent, the cylindrical stent being subjected to heat treatment, wherein the cylindrical stent has a first artificial blood vessel layer made of a polytetrafluoroethylene (PTFE) material and being in entire contact with an inner surface of the cylindrical stent, and a plurality of second artificial blood vessel layers made of the PTFE material and being in partial contact with an outer surface of the cylindrical stent at predetermined intervals, and the first artificial blood vessel layer and the plurality of second artificial blood vessel layers are fused together by heat fusion to encompass the cylindrical stent, thereby forming a plurality of first sections having a plurality of openings obstructed and a plurality of seconds sections having the plurality of openings remaining unobstructed, wherein the first sections are inserted into the lesion while pressing against the lesion, thereby being caught in the lesion, and the second sections are caught in the lesion that is meshed with the openings.

Advantageous Effects

As described above, according to the present invention, the first sections are inserted into the lesion while pressing against the lesion, thereby being caught in the lesion, and the second sections are caught in the lesion that is meshed with the openings remaining unobstructed. Consequently, it is possible to prevent the stent from slipping at the lesion due to movement of the human body or an external force.

In other words, since the first and second sections of the stent are caught in the lesion in a double manner in different shapes, the anti-slip function can be improved as compared with the conventional art.

According to the present invention, the obstructed openings of the first sections are prevented from deformation in shape due to an external force applied upon insertion of the stent, whereas the unobstructed openings of the second sections are deformed in shape due to the external force applied upon insertion of the stent. Consequently, it is possible to curve the stent to agree with the shape of a curved lumen of the body.

According to the present invention, the first sections are configured to have the same length, and the second sections are configured to have the same length. Consequently, the first and second sections can be caught in the lesion to occupy the same area, respectively.

In addition, the stent can be curved in a shape to agree with a certain curved shape of a curved lumen of the body, and maintain the curved shape by the first sections that exert the same supporting force.

According to the present invention, the first sections are configured to have the same length, and the second sections are configured to have different lengths. Consequently, the first sections can be caught in the lesion to occupy the same area, and the second sections can be caught in the lesion to occupy different areas.

In addition, the stent can be curved in various shapes to agree with a lumen of the body having various curved shapes, and maintain the curved shape by the first sections that exert the same supporting force.

According to the present invention, the first sections are configured to have different lengths, and the second sections are configured to have the same length. Consequently, the first sections can be caught in the lesion to occupy different areas, and the second sections can be caught in the lesion to occupy the same area.

In addition, the stent can be curved in a shape to agree with a certain curved shape of a curved lumen of the body, and maintain the curved shape by the first sections that exert different supporting forces.

BEST MODE

Hereinafter, exemplary embodiments of the present invention will be described in detail with reference to the accompanying drawings.

Figure 1:
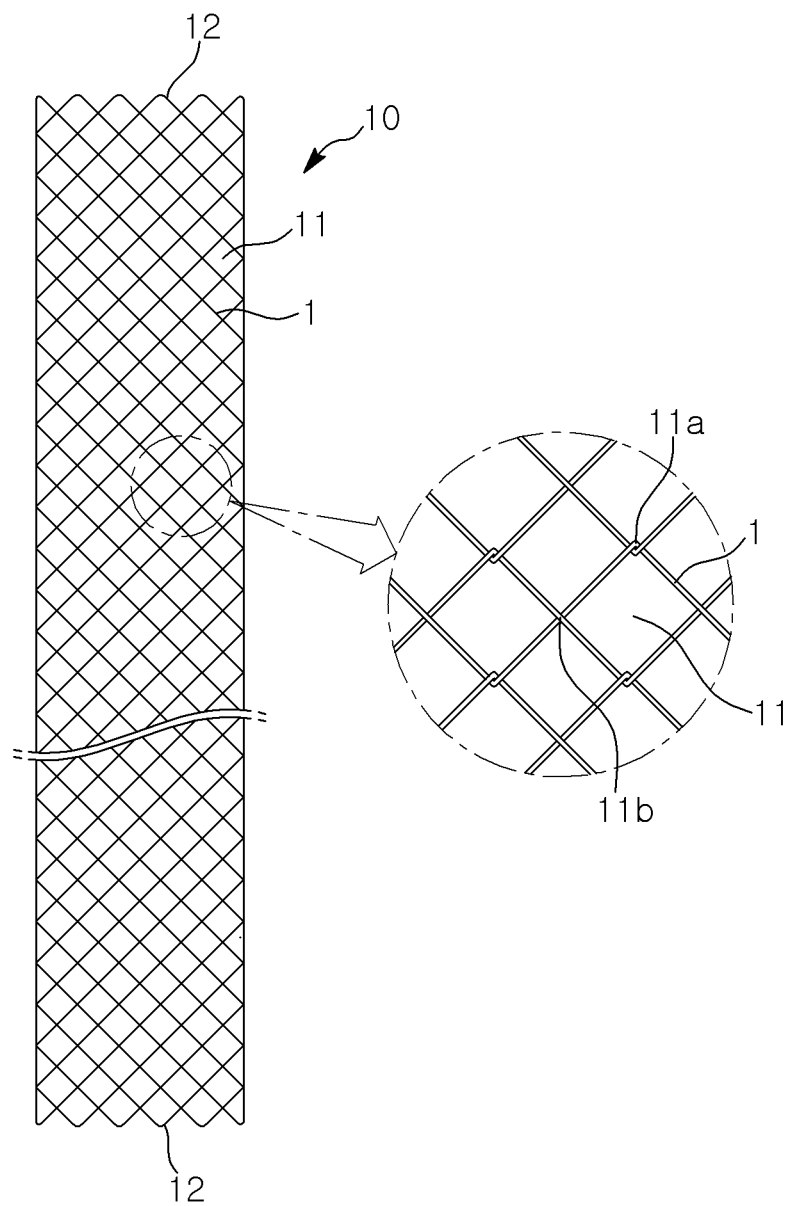
FIG. 1 is a front view showing a cylindrical stent according to an embodiment of the present invention.

A stent 100 with an improved anti-slip function according to an embodiment of the present invention is configured to widen a lesion such as stenosis or occlusion in a lumen of the body, and as shown in FIG. 1, includes a cylindrical stent 10 including a plurality of rhombic openings 11 formed by weaving wires made of a super-elastic shape memory alloy in a hollow cylindrical mesh shape in an interlocking or intersecting manner, and a plurality of peaks 12 circumferentially provided at opposite corrugated ends of the cylindrical stent, the cylindrical stent being subjected to heat treatment.

Herein, interlocking portions 11a where the wires 1 interlock each other, and interlocking portions 11b where the wires 1 intersect each other are provided at the peripheries of the openings 11.

Figure 2:
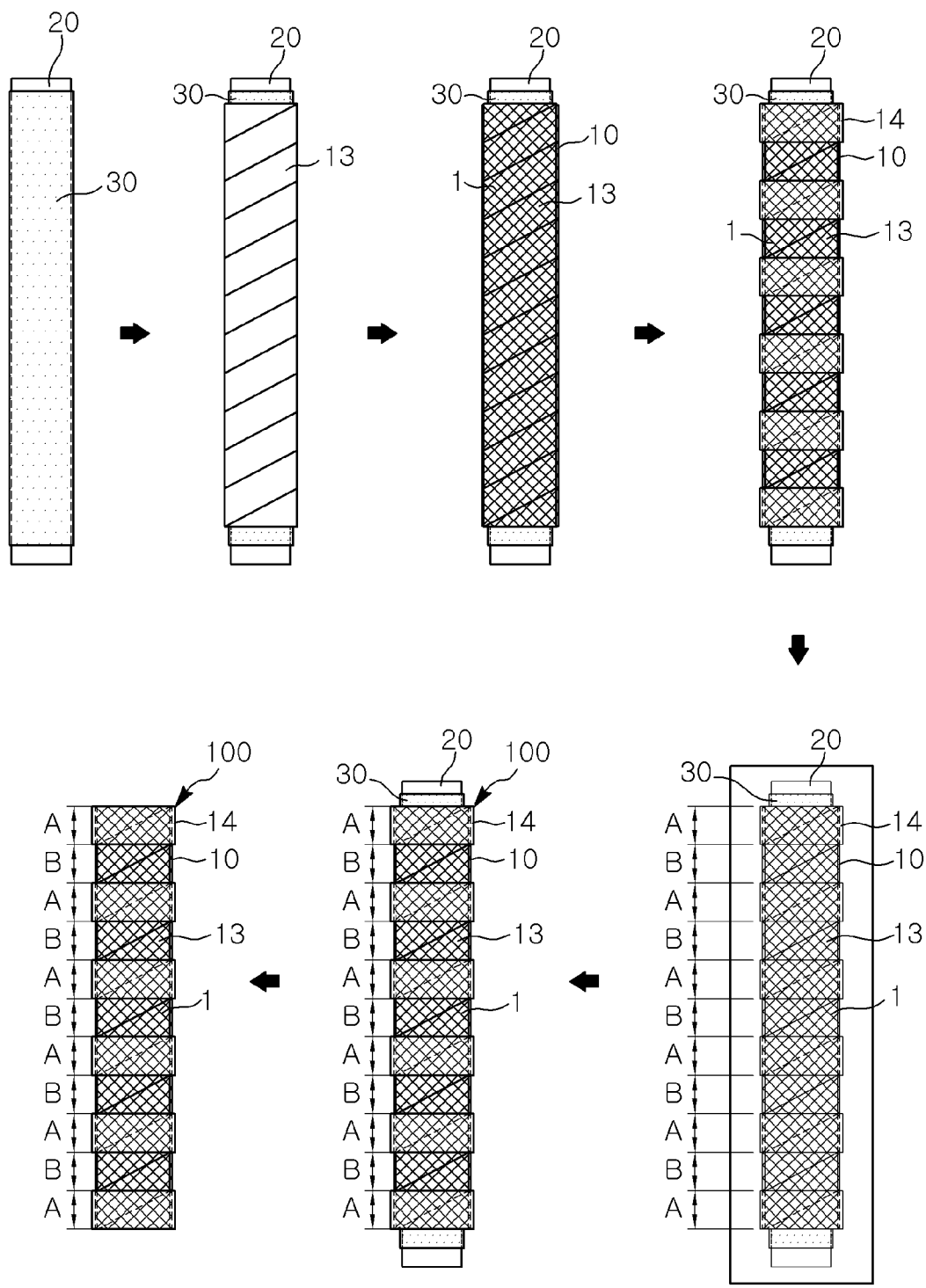
FIG. 2 is a process flow diagram showing a stent with an improved anti-slip function according to the embodiment of the present invention.

Further, as shown in FIG. 2, for producing the stent 100 with the improved anti-slip function, a jig 20 that has a size the same as or a size similar to an inner diameter of the cylindrical stent 10 is prepared.

Thereafter, a first artificial blood vessel layer made of a polytetrafluoroethylene (PTFE) material is wound on an outer surface of the jig 20 in a lengthwise direction of the jig 20 in a taping manner, and then the jig 20 is inserted into the cylindrical stent 10.

Then, second artificial blood vessel layers 14 made of a polytetrafluoroethylene (PTFE) material are separately wound on an outer surface of the cylindrical stent 10 in a taping manner such that the second artificial blood vessel layers are positioned at predetermined intervals in the lengthwise direction of the cylindrical stent 10.

Herein, the second artificial blood vessel layers 14 separately wound on the cylindrical stent 10 remain the same in length.

Accordingly, the cylindrical stent 10 has the first artificial blood vessel layer 13 made of the PTFE material and being in entire contact with the inner surface of the cylindrical stent 10, and a plurality of second artificial blood vessel layers 14 made of the PTFE material and being in partial contact with the outer surface of the cylindrical stent at predetermined intervals.

Thereafter, the cylindrical stent 10 having the first and second artificial blood vessel layers 13 and 14 on the inner and outer surfaces thereof is put into a heat-pressing device together with the jig 20, and is then applied with heat and pressure.

Accordingly, the first artificial blood vessel layer 13 and the plurality of second artificial blood vessel layers 14 are fused together by heat fusion to encompass the cylindrical stent 10, thereby producing the stent 100 including a plurality of first sections A having a plurality of openings 11' obstructed and a plurality of second sections B having a plurality of openings 11 remaining unobstructed.

Herein, the first sections A are configured to have the same length, and the second sections B are configured to have the same length.

In addition, the openings 11' of the first sections A are obstructed by the first and second artificial blood vessel layers 13 and 14 that are fused together, whereas the openings 11 of the second sections B remain unobstructed because the first artificial blood vessel layer 13 remains unfused due to absence of the second artificial blood vessel layers 14 that are fused with the first artificial blood vessel layer.

Then, the stent 100 having the jig 20 fitted therein is taken out from the heat-pressing device, and the stent 100 is separated from the jig 20.

Figure 3:
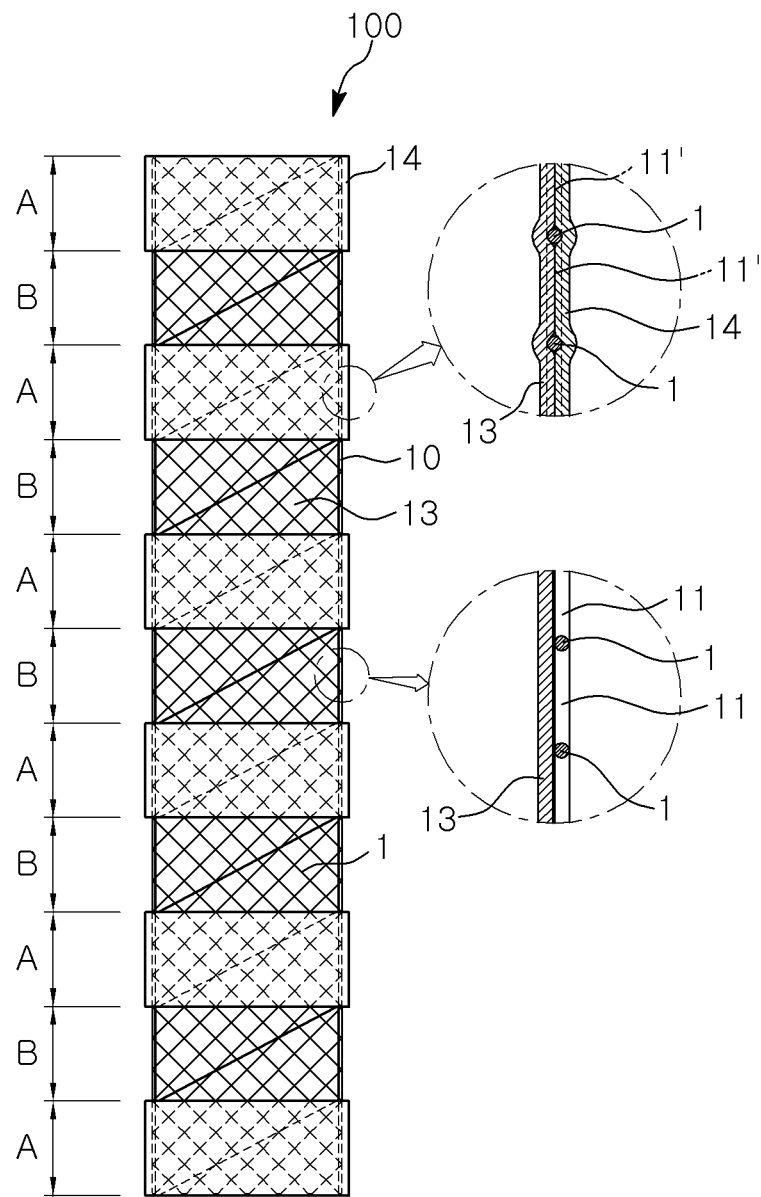
FIG. 3 is a front view showing the stent with the improved anti-slip function according to the embodiment of the present invention.

As a result, as shown in FIG. 3, the stent 100 with the improved anti-slip function according to the embodiment of the present invention is produced such that the first sections A are inserted into a lesion while pressing against the lesion, thereby being caught in the lesion, and the sections B are caught in the lesion that is meshed with the openings 11.

Moreover, since the openings 11' of the first sections A are fixed to the first and second artificial blood vessel layers 13 and 14 that are fused together, even when an external force is applied to the first sections, the openings of the first sections are prevented from deformation in shape, whereas since the openings 11 of the second sections B are not fixed to the first artificial blood vessel layer 13 that remains unfused due to absence of the second artificial blood vessel layers 14 that are fused with the first artificial blood vessel layer, when the external force is applied to the second sections, the openings of the second sections are deformed in shape.

Figure 4:
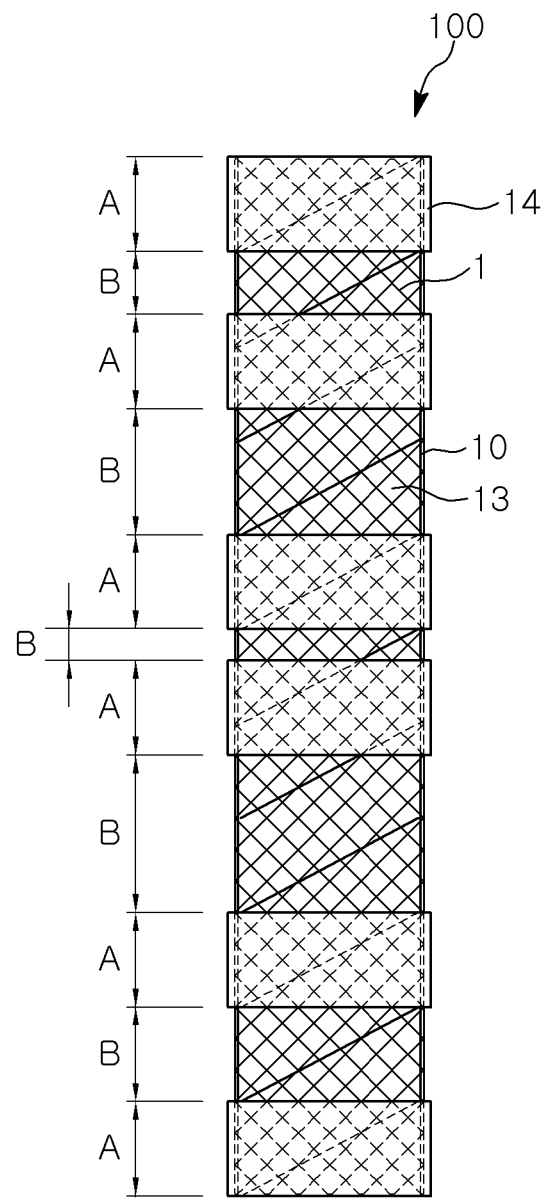
FIGS. 4 and 5 are front views showing a stent with an improved anti-slip function according to another embodiment of the present invention.

Meanwhile, as shown in FIG. 4, a stent 100 according to another embodiment of the present invention may be configured such that first sections A are configured to have the same length, and second sections B are configured to have different lengths.

In other words, the second artificial blood vessel layers 14 are wound separately in a taping manner on a part of the outer surface of the cylindrical stent 10 such that the second artificial blood vessel layers have the same length, wherein the second artificial blood vessel layers 14 are arranged at different intervals.

Figure 5:
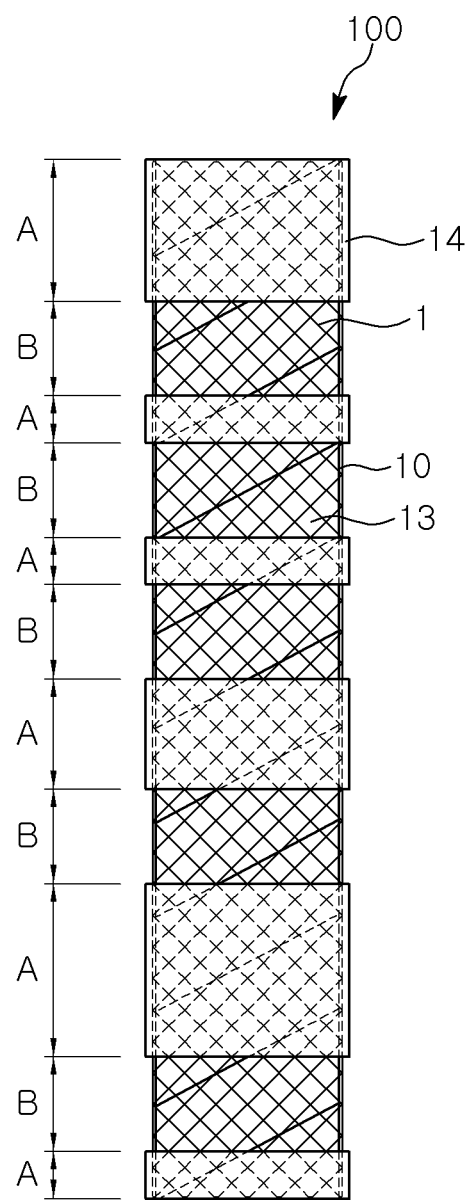

Further, as shown in FIG. 5, a stent 100 according to another embodiment of the present invention may be configured such that second sections B are configured to have the same length, and first sections A are configured to have different lengths.

In other words, the second artificial blood vessel layers 14 are wound separately in a taping manner on a part of the outer surface of the cylindrical stent 10 such that the second artificial blood vessel layers have different lengths, wherein the second artificial blood vessel layers 14 are arranged at the same interval.

The operation and effect of the stent 100 with the improved anti-slip function as described above will be described as follows.

As shown in FIGS. 1 to 3, and FIG. 6, the stent 100 according to the embodiment of the present invention is inserted into a lesion such as stenosis or occlusion occurring in a lumen of the body such as the esophagus, the duodenum, or the bile duct using a stenting device, and widens the lesion such as stenosis or occlusion.

Further, the first sections A are inserted into the lesion while pressing against the lesion, thereby being caught in the lesion, and the second sections B are caught in the lesion that is meshed with the openings 11.

Herein, as shown in FIG. 3, the stent 100 is configured such that the first sections A are configured to have the same length, and the second sections B are configured to have the same length.

In other words, the first sections A are inserted into the lesion while pressing against the lesion, thereby being caught in the lesion to occupy the same area, and the second sections B are caught in the lesion, which is meshed with the openings 11, to occupy the same area.

Herein, the first sections A are inserted into the lesion while pressing against the lesion by the thickness of the second artificial blood vessel layers 14 made of a PTFE material, thereby being caught in the lesion.

Further, since the first sections A arranged with the second sections B interposed therebetween have the first and second artificial blood vessel layers 13 and 14 that are fused together, the PTFE-first artificial blood vessel layer 13 of the second sections B is supported by the first and second artificial blood vessel layers 13 and 14 of the first sections A.

Accordingly, the lesion is prevented from intruding into the openings 11 of the second sections B, pushing the first artificial blood vessel layer 13 of the second sections B, and protruding to the inside of the stent 100.

In other words, the lesion is prevented from protruding to the inside of the stent 100, thereby being prevented from bleeding due to tearing by the wires 1 of the peripheries of the openings 11 of the second sections B.

Figure 6:
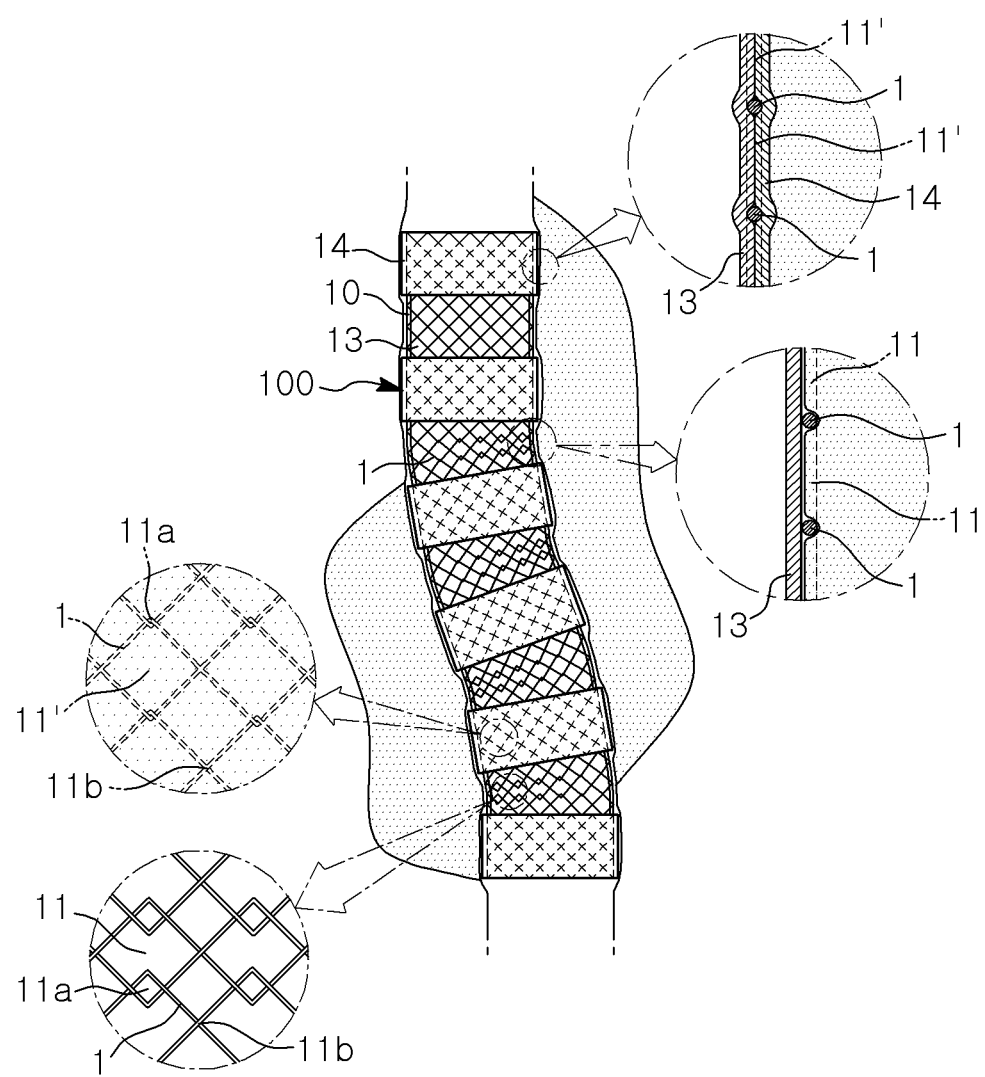
FIG. 6 is a view showing a use state of the stent with the improved anti-slip function according to the embodiment of the present invention.

Further, as shown in FIG. 6, the second sections B of the stent 100 are curved when the plurality of openings 11 is deformed in shape in response to a shape of a lumen in the body.

In other words, since the openings 11 of the second sections B are not fixed to the first artificial blood vessel layer 13 that remains unfused due to absence of the second artificial blood vessel layers 14 that are fused with the first artificial blood vessel layer, the openings of the second sections are deformed in shape by an external force exerting thereon when the stent 100 is inserted into a lumen of the body.

Thus, the stent 100 is placed into the lesion to have the same curved shape as that of a curved lumen of the body.

Herein, since the openings 11' of the first sections A are fixed to the first and second artificial blood vessel layers 13 and 14 that are fused together, the openings of the first sections are prevented from deformation in shape. Accordingly, the second sections B of the stent 100 maintain the curved shape to agree with the shape of a curved lumen of the body.

Meanwhile, as shown in FIG. 4, a stent 100 according to another embodiment of the present invention is configured such that first sections A are configured to have the same length, and second sections B are configured to have different lengths.

In other words, the first sections A are inserted into the lesion while pressing against the lesion, thereby being caught in the lesion to occupy the same area, and the second sections B are caught in the lesion, which is meshed with the openings 11, to occupy different areas.

In addition, the stent 100 has a curved shape different from that of the stent 100 of FIG. 6, and maintains the curved shape by the first sections A that exert the same supporting force.

Further, as shown in FIG. 5, a stent 100 is configured such that second sections B are configured to have the same length, and first sections A are configured to have different lengths.

In other words, the first sections A are inserted into the lesion while pressing against the lesion, thereby being caught in the lesion to occupy different areas, and the second sections B are caught in the lesion, which is meshed with the openings 11, to occupy the same area.

Moreover, the stent 100 has a curved shape the same as that of the stent 100 of FIG. 6, and maintains the curved shape by the first sections A that exert different supporting forces.

Although a preferred embodiment of the present invention has been described for illustrative purposes, those skilled in the art will appreciate that various modifications, additions and substitutions are possible, without departing from the scope and spirit of the invention as disclosed in the accompanying claims.

DESCRIPTION OF THE REFERENCE NUMERALS IN THE DRAWINGS

10: cylindrical stent 11,11': opening
12: peak
13: first artificial blood vessel layer
14: second artificial blood vessel layer
20: jig
100: stent

The invention claimed is:

1. A stent with an improved anti-slip function, the stent being configured to widen a lesion such as stenosis or occlusion in a lumen of a body, and comprising:
 a cylindrical stent including a plurality of rhombic openings formed by weaving wires made of a super-elastic shape memory alloy in a hollow cylindrical mesh shape in an interlocking or intersecting manner, and a plurality of peaks circumferentially provided at opposite corrugated ends of the cylindrical stent, the cylindrical stent being subjected to heat treatment,
 wherein the cylindrical stent has a first artificial blood vessel layer made of a polytetrafluoroethylene (PTFE) material and being in entire contact with an inner surface of the cylindrical stent, and a plurality of second artificial blood vessel layers made of the PTFE material and being in contact with an outer surface of the cylindrical stent at predetermined intervals, and
 the first artificial blood vessel layer and the plurality of second artificial blood vessel layers are fused together by heat fusion to encompass the cylindrical stent, thereby forming a plurality of first sections having a plurality of obstructed openings and a plurality of second sections having a plurality of unobstructed openings.

2. The stent of claim 1, wherein the openings of the first sections are fixed to the first and second artificial blood vessel layers that are fused together, so that even when an external force is applied to the first sections, the openings of the first sections are prevented from deformation in shape, and the openings of the second sections are not fixed to the first artificial blood vessel layer that remains unfused due to absence of the second artificial blood vessel layers that are fused with the first artificial blood vessel layer, so that when the external force is applied to the second sections, the openings of the second sections are deformed in shape.

3. The stent of claim 1, wherein the first sections are configured to have the same length and the second sections are configured to have the same length.

4. The stent of claim 1, wherein the first sections are configured to have the same length and the second sections are configured to have different lengths.

5. The stent of claim 1, wherein the second sections are configured to have the same length, and the first sections are configured to have different lengths.

6. The stent of claim 2, wherein the first sections are configured to have the same length and the second sections are configured to have the same length.

7. The stent of claim 2, wherein the first sections are configured to have the same length and the second sections are configured to have different lengths.

8. The stent of claim 2, wherein the second sections are configured to have the same length, and the first sections are configured to have different lengths.

* * * * *